United States Patent
Harichian et al.

(10) Patent No.: US 11,059,776 B2
(45) Date of Patent: Jul. 13, 2021

(54) METHOD OF ENHANCED CONVERSION OF TAURINE SALTS TO ALKYL TAURATE AMIDES

(71) Applicant: Conopco, Inc., Trumbull, CT (US)

(72) Inventors: Bijan Harichian, Irvine, CA (US); Van Au, Oxford, CT (US); Anat Shiloach, Trumbull, CT (US); John Robert Winters, Dumont, NJ (US); Erin Whitfield Dunn, San Francisco, CA (US)

(73) Assignee: CONOPCO, INC., Englewood Cliffs, NJ (US)

( * ) Notice: Subject to any disclaimer, the term of this patent is extended or adjusted under 35 U.S.C. 154(b) by 0 days.

(21) Appl. No.: 16/649,784

(22) PCT Filed: Sep. 24, 2018

(86) PCT No.: PCT/EP2018/075747
§ 371 (c)(1),
(2) Date: Mar. 23, 2020

(87) PCT Pub. No.: WO2019/068494
PCT Pub. Date: Apr. 11, 2019

(65) Prior Publication Data
US 2020/0283379 A1 Sep. 10, 2020

(30) Foreign Application Priority Data
Oct. 3, 2017 (EP) .................................... 17194640

(51) Int. Cl.
*C07C 303/22* (2006.01)
*C07C 309/14* (2006.01)
*C07C 309/15* (2006.01)

(52) U.S. Cl.
CPC .......... *C07C 303/22* (2013.01); *C07C 309/14* (2013.01); *C07C 309/15* (2013.01)

(58) Field of Classification Search
CPC .... C07C 303/22; C07C 309/15; C07C 309/14
See application file for complete search history.

(56) References Cited

U.S. PATENT DOCUMENTS

| | | | |
|---|---|---|---|
| 2,880,219 A | 3/1959 | Burnette | |
| 3,150,156 A | 9/1964 | Lamberti | |
| 3,232,968 A * | 2/1966 | Nunn, Jr. | C07C 309/15 554/49 |
| 5,496,959 A * | 3/1996 | Day | C07C 303/32 554/49 |

FOREIGN PATENT DOCUMENTS

| | | |
|---|---|---|
| CN | 106588710 | 4/2017 |
| JP | 2002234868 | 8/2002 |
| WO | WO2018059889 | 4/2018 |

OTHER PUBLICATIONS

IPRP2 in PCTEP2018075747; dated Jan. 7, 2020.
Written Opinion 2 for PCTEP2018075747; dated Aug. 28, 2019.
Search Report and Written Opinion in EP17194640; dated Mar. 2, 2018.
Search Report and Written Opinion in PCTEP2018075747; dated Dec. 21, 2018.
Search Report and Written Opinion in EP18169068; dated Oct. 12, 2018
Search Report and Written Opinion in PCTEP2019058706; dated Jul. 10, 2019.
Burnette et al.; Reaction of Fatty Acids with N-Methyl Taurine. Mar. 23, 1962. pp. 1-2.
Co-pending Application, Serial No. 18169068.6.

\* cited by examiner

*Primary Examiner* — Yate' K Cutliff
(74) *Attorney, Agent, or Firm* — Krista A. Kostiew

(57) ABSTRACT

The invention relates to a method of enhancing conversion of alkali metal salt, preferably aqueous salt, preferably aqueous sodium salt of N-methyl taurine to alkyl taurate amides. In one aspect, the starting salt is pre-concentrated (at least 75% up to 99% taurine salt in the aqueous solutions after water is removed from a starting aqueous solution of the salt) and, in another aspect, the starting salt is not pre-concentrated.

16 Claims, No Drawings

METHOD OF ENHANCED CONVERSION OF TAURINE SALTS TO ALKYL TAURATE AMIDES

CROSS REFERENCE TO RELATED APPLICATIONS

The present application is a U.S. National Phase Application under 35 U.S.C. § 371 of International Application No. PCT/EP2018/075747, filed on Sep. 24, 2018, which claims priority to European Patent Application No. 17194640.3, filed on Oct. 03, 2017, the contents of which are incorporated herein in their entireties.

FIELD OF THE INVENTION

The present invention relates to a method or process for enhancing yield and reducing risk of browning of alkyl taurate amides ("ATA") which are typically made from amidation reaction of salts of N-methyl taurine, preferably aqueous salts of N-methyl taurine with fatty acid (e.g., $C_8$ to $C_{24}$, preferably $C_8$ to $C_{16}$ chain length fatty acid).

BACKGROUND OF THE INVENTION

There are many parameters involved in the amidation reaction in which typically taurine and/or taurine salts react with fatty acid to produce ATA.

Among those parameters which affect both the yield and the appearance (e.g., whether the product suffers from undesirable browning) are the ratio of fatty acid to taurine or salt of taurine; the time and temperature of the reaction; and the amount of catalyst (typically, a catalyst such as zinc oxide, magnesium oxide or hypophosphorous acid, $H_3PO_2$ is used for such reactions). Whether the taurine is branched (e.g., with methyl or other alkyl group) may also affect the reaction. Typically, in the absence of any particular guidance, yield of ATA ranges from about 50% to 75% or 80% yield. There is no teaching, as far as applicants are aware, of how to consistently ensure that higher yields (e.g., at least about 80%, preferably 80% or more) are obtained.

U.S. Pat. No. 5,496,959 to Day relates to preparation of N-acyl taurates by reaction of carboxylic acid with "taurate" derivatives (defined as substituted 2-aminoalkane sulfonic acids and their alkali metal salts).

There is no particular disclosure of what should be the ratios (i.e., molar ratio) of fatty acid to taurine or of the other variables noted above. For example, Example 1 uses 340.8 g stearic acid to 396.8 g sodium N-methyl taurate solution (37.1%); this is a molar ratio of 1.3:1 fatty acid to taurine, less than the 1.5:1 fatty acid to taurine ratio of our invention; there is also no disclosure of the criticality, if any, of the amount of catalyst; and there is no disclosure of the criticality of reaction time. Reaction temperature may be up to 205° C.

U.S. Pat. No. 2,880,219 to Burnette also teaches production of N-acyl taurides from fatty acids and taurines. From the table at column 7, it is seen that yields are generally higher when temperatures are typically at or above 220° C. and require long reaction time (10 hours) due to the fact that no reaction catalyst was employed. There is certainly no recognition regarding criticality in amount of catalyst used, for example. Also, there is not used specifically salt, preferably a solution comprising an aqueous salt of N-methyl taurine as starting reactant. As will be seen from our invention, parameters are very sensitive, so it would be difficult to predict the difference in performance if using taurine versus N-methyl taurine, let alone other criticalities in ratios of fatty acid to taurine; or in amounts of catalyst.

"Reaction of Fatty Acids with N-Methyl Taurine" to Burnette and Chiddix also discloses a similar reaction. Temperatures of reaction all seem to be well over 200° C. There is again no criticality recognized regarding use or range of catalyst.

JP 2002-234868 to Rekkutekku describes a process for making acyl taurate by reacting fatty acid with taurine. The reaction uses solid taurine, and not salts of N-methyl taurine, preferably aqueous salts of N-methyl taurine. As noted, it is very difficult to predict which parameters, including type of taurine or derivative, provide optimal production of taurate in good yield with little or no browning.

U.S. Pat. No. 3,232,968 to Schenck et al. discloses process for preparing N-acyl taurates using hypophosphorous acid. There is no recognition of criticality of combination of molar ratio; temperature range, reaction time and range of catalyst. For example, Example 1 is conducted at higher temperatures than our invention; and molar ratios of fatty acid to taurine in Examples 2 and 3 is less than 2:1.

It would thus be extremely beneficial and desirable to have a process where it was possible to consistently obtain high yields when reacting fatty acid and taurines while maintaining excellent product appearance (e.g., no browning), particularly since browning leads to an unacceptable appearance in the consumer product.

SUMMARY OF THE INVENTION

In one aspect, applicants have discovered that by using salts of taurine e.g. salts of N-methyl taurine, and by controlling parameter ranges within certain critical ranges, applicants can consistently obtain yields of ATA of at least about 80%, preferably 80% or above, all while avoiding browning. The salt can be solid but is preferably an aqueous salt of taurine, more preferably aqueous salts of N-methyl taurine.

In a second aspect, applicants have found that pre-concentrating salt of N-methyl taurine (e.g., removing water so taurine salt is at least 75%, preferably 80% or 85%, more preferably 90% up to 99% or 98%, but less than 100% of the aqueous solution) is an especially preferred parameter, and that it is possible to obtain high yield as defined above, in the absence of browning, using parameters that are even less restrictive (e.g., in range of catalyst) than those defined for the first aspect of the invention. Pre-concentration is done through removal of water from an aqueous salt; applicants have unexpectedly discovered such pre-concentration to be critical parameter of a second aspect of the invention) The invention also relates to alkyl taurate amides obtainable by either process of the invention.

DETAILED DESCRIPTION OF THE INVENTION

Except in the examples, or where otherwise explicitly indicated, all numbers in this description indicating amounts of material or conditions of reaction, physical properties of materials and/or use are to be understood as modified by the word "about."

As used throughout, ranges are used as shorthand for describing each and every value that is within the range. Any value within the range can be selected as terminus of the range. The use of and/or indicates that any one from the list can be chosen individually, or any combination from the list can be chosen.

For the avoidance of doubt, the word "comprising" is intended to mean "including" but not necessarily "consisting of" or "composed of." In other words, the listed steps or options need not be exhaustive.

Unless indicated otherwise, all percentages for amount or amounts of ingredients used are to be understood to be percentages by weight based on the active weight of the material in the total weight of the composition, which total is 100%.

The present invention relates to a process for enhancing conversion of taurine, particularly salts of N-methyl taurine, to alkali taurate amides. In one aspect, the process does not involve a pre-concentration step; and, in a second aspect there is a pre-concentration step. The pre-concentration step allows slightly less restrictive parameters to be used while still obtaining high yields as defined.

As indicated, in one aspect, the invention relates to reaction in which a fatty acid is reacted (e.g., $C_8$ to $C_{22}$ or $C_8$ to $C_{20}$, fatty acid, preferably straight chain and saturated; preferably $C_{10}$ to $C_{18}$ fatty acid, again preferably straight chain and saturated; more preferably $C_{10}$ to $C_{14}$ fatty acid). More specifically, fatty acid is reacted with with a salt, preferably an aqueous salt of N-methyl taurine at defined molar ratios of fatty acid to the taurine salt. If more than one fatty acid is used, the ratio is defined as the molar ratio of all fatty acid in the mixture to taurine salt. The reaction takes place in the presence of a catalyst and should be run at defined reaction temperature for a defined reaction time.

As indicated, use of $C_{10}$ to $C_{14}$, particularly $C_{12}$ fatty acid is highly preferred when using range of $C_8$ to $C_{22}$, or $C_8$ to $C_{20}$ fatty acid. For example, 50 to 100% is preferably $C_{10}$ to $C_{14}$ and preferably $C_{12}$ fatty acid. In a more preferred situation, 100% of the fatty acid may be $C_{12}$, i.e., $C_{12}$ is the sole reacting fatty acid.

According to this first aspect of the invention, the starting taurine salt is not pre-concentrated. When using pre-concentration in a second aspect of the invention, this means that taurine salt remains in an amount of at least 75%, preferably at least 80% or 85%, more preferably 90% or more, but less than 100% of the overall solution of taurine in water. For the not-preconcentrated situation, this could mean the starting taurine salt is an aqueous salt but not pre-concentrating. It then remains very watery. Or, the starting taurine salt is solid. Non-preconcentrating then means that the taurine salt is such solid and there was no need to pre-concentrate.

By maintaining very specific parameters relating to ratios, reaction temperatures, reaction time and amount of catalyst, applicants have unexpectedly found they can consistently produce yield of 80% or more while avoiding undesirable browning.

More particularly, in this first aspect of the invention (where no pre-concentration is required), the invention comprises a process for preparation of ATA comprising the step of reacting of fatty acid or mixture of fatty acid (a preferred fatty acid is $C_{12}$ straight chain fatty acid) with a salt (e.g., alkali metal salt such as sodium or potassium salt), preferably aqueous salt of N-methyl taurine wherein
 a) the molar ratio of total fatty acid to alkali metal salt of N-methyl taurine, both measured on an anhydrous basis, is greater or equal to 2:1, preferably 2:1 to 5:1;
 b) reaction temperature is less than 200° C., preferably 190 to 199° C.;
 c) catalyst (e.g., ZnO and/or other noted catalysts) is used in an amount ranging from 0.4 to 0.7% by wt.; and
 d) time of reaction is two hours or greater, preferably 2 to 4 hours or 2 to 3 hours.

The level of catalyst (0.4 to 0.7% by wt.) is the weight percent based on total reaction mixture on an anhydrous basis, e.g., anhydrous weight of N-methyl taurine plus weight of fatty acid plus weight of catalyst. For example, 25 grams of 55% solution of N-methyl taurine has 13.75 g of N-methyl taurine on an anhydrous basis.

The sensitivity to the various variables can be seen, for example, when observing results of Examples 1 to 9 as well as Comparative Examples A to K in the Examples sections of the specification.

In Comparative Example B, for example, (non-concentrated salt of N-methyl taurine used), where the molar ratio of free fatty acid (only $C_{12}$ is used in that example) to taurine salt is 2:1, but where catalyst (ZnO) is used at 1% (i.e., above 0.4 to 0.7% criticality), conversion rate is 55%. Similarly, in Comparative C (again with non-concentrated salt of N-methyl taurine), where catalyst is now used at 0.5% (within parameters of our invention), but the ratio of fatty acid to taurine salt is now 1.5:1 (i.e., below 2:1 ratio of claims), conversion rate is below 80% (62.1% conversion).

In Examples 5 and 6, however, where now both ratios of fatty acid to taurine salt and catalyst levels are within the claims of the invention, conversion rates are 81% and 86.5%, respectively. Comparative G has a ratio of 2:1 and lower level of catalyst (0.3% ZnO is below claimed amounts of 0.4) and, again, conversion rate is below 80%, i.e., at 72.2%.

In a second aspect of the invention, the invention relates to the same reaction for combining fatty acid (with chain length as defined in first aspect) and salt of N-methyl taurine. In this aspect, the taurine salt is pre-concentrated (e.g., to at level of 75% or greater, preferably 80 or 85% or, more preferably 90% or more, but less than 100% salt of N-methyl taurine, e.g., the salt is not "solid").

According to this aspect of the invention the criticalities can be kept slightly broader (e.g., broader range of catalyst) while obtaining the same high yield (80% or more), and while avoiding undesirable browning.

More particularly, this aspect of the invention (where pre-concentrate is required) comprises a process for preparing ATA comprising the step of reacting fatty acid (one fatty acid or mixture of fatty acids can be used) with aqueous salt of N-methyl salt, wherein the aqueous taurine salt is first pre-concentrated and then combined with fatty acid or mixtures of fatty acid; and, wherein
 a) either the molar ratio of fatty acid or mixture of fatty acid to salt of N-methyl taurine is greater than 1.5:1, or the time of reaction is greater than or equal to 2 hours (e.g., molar ratio of fatty acid to taurine can be 1.5 or less, if time of reaction is at least 2 hours, see Example 1; or time of reaction can be less than 2 hours, if fatty acid to taurine ratio is greater than 1.5, see Example 2);
 b) the catalyst level is 0.1 to 1.5 wt. %, preferably 0.5 to 1.5 wt. %, more preferably 0.8 to 1.2 wt. %; and
 c) temperature of the reaction is less than 200° C., preferably 190 to 199° C.

The level of catalyst is the same as defined in the first aspect of the invention.

Again, the sensitivity of these variables can be seen from the examples.

For example, as noted, when pre-concentrating to 90% salt of N-methyl taurine, even if fatty acid to taurine ratio not above 1.5, yield is still greater than 80% (82%), if reaction time is two hours or more, e.g., 2 to 4 hours (see Example 1). Conversely, even if reaction time of one hour, yield of greater than 80% (83%) is reached when molar ratio of fatty acid to taurine salt, both measured on an anhydrous basis, is 1.5 or greater (e.g., 2 to 1, as in Example 2).

The fatty acids used in the process of both or either aspect of the invention are typically $C_8$ to $C_{22}$, preferably straight chain, saturated fatty acids. Preferably, these fatty acids are $C_{10}$ to $C_{18}$, more preferably $C_{10}$ to $C_{14}$ fatty acids. If more than one fatty acid is used, then the ratio is molar ratio of all fatty acids to taurine.

The fatty acid reacts with taurine salt, e.g., $NH_2CH_2CH_2SO_3^-$ $M^+$ where $M^+$ may be a sodium or potassium counterion.

The molar ratio of fatty acid or of total fatty acids to taurine salt (both on anhydrous basis) in the first aspect (non-concentrated taurine salt) is greater or equal to 2:1, preferably 2:1 to 5:1.

In the second aspect (using concentrated taurine salt), the ratio of fatty acid to taurine salt is typically greater than 1.5:1; however, it can also be 1.5:1 or less if the reaction time is 2 hours or greater (e.g., 2 to 4 hours).

The reaction temperature in either aspect of the invention is less than 200° C., preferably 190 to 199° C.

The reaction time in the first aspect of the invention is two hours or greater, preferably 2 to 4 hours. In the second aspect, reaction time can be less than 2 hours (for example, as low as 1 hour) if fatty acid to taurine ratio is greater than 1.5.

A wide variety of catalysts can be employed with the present reaction. Suitable catalysts include multivalent metal ion salts or organic or inorganic compounds, strong acids and mixtures thereof. Alkali metal oxide catalysts may be used. Examples include zinc oxide, magnesium oxide and calcium oxide. Zinc oxide, a preferred catalyst, can be utilized in this invention. However, faster acting catalysts are preferred. Among the fast organic catalysts is zinc isethionate. Especially preferred inorganic zinc compounds are those selected from the group consisting of zinc sulfate, zinc sulfamate, and zinc oxide acidified with sulfamic or sulfonic acid. Other catalysts which may be used include, but are not limited to, phosphorous based catalysts. Such catalysts include hypophosphorous acid ($H_3PO_2$), sodium hypophosphite, phosphoric acid, triphosphoric acid, polyphosphoric acid ($H_3PO_4$), and mixtures thereof.

As noted, mixtures of the aforementioned compounds may also be employed.

In the first aspect of the invention (no pre-concentration), catalyst is present at about 0.4 to 0.7% by wt. In the second aspect of the invention (pre-concentration) catalyst can be used at level of 0.1 to 1.5%, preferably 0.5 to 1.5%, more preferably 0.8 to 1.2%.

Process

Typical process is set forth below.

1. In a four necks 250 ml round bottom flask, equipped with mechanical stirrer, condenser, solvent trap/receiver and thermocouple/nitrogen ($N_2$) flow inlet, sodium N-methyl taurine (25 g, 55% solution, 1 eq.) was added. The $N_2$ flow was set to 0.2 liter per minute (LPM). The solution of N-methyl taurine was heated to about 150° C. to remove water to about 90% taurine concentration.
2. The reaction temperature was increased to about 195° C., and lauric acid (51.29 g, 3 eq.) and zinc oxide (0.66 g, 1%.) were added. The reaction mixture stirred at 195° C. for one to four hours.

EXAMPLES

Examples 1 and 2 and Comparatives B, C and D show the effect of pre-concentrate (removal of water) on final conversion rate. This is set forth below.

1. Effect of Taurine Concentration (Water Removal) of N-Methyl Taurine Salt on Conversion:

| Example # | C12 fatty acid/ taurine ratio | ZnO use % | Taurine salt pre-concentration at 150 C. | Rx temperature (C.) | Rx time (Hr) | % conversion C12 taurate |
|---|---|---|---|---|---|---|
| Comparative A | 1.5 to 1 | 1 | No, 55% | 197 | 2 | 71 |
| Example 1 | 1.5 to 1 | 1 | Yes, to 90% | 197 | 2 | 82 |
| Comparative B | 2 to 1 | 1 | No, 55% | 197 | 3 | 55 |
| Example 2 | 2 to 1 | 1 | Yes, to 90% | 197 | 1 | 83 |
| Comparative C | 1.5 to 1 | 0.5 | No, 61% | 195 | 3 | 62.1 |
| Comparative D | 1.5 to 1 | 0.5 | Yes, to 73% | 195 | 3 | 71.6 |

In these examples, Examples 1 and 2 were pre-concentrated to 90% and Comparative D to only 73%. It can be seen that, the conversion rate was above 80% in both cases where pre-concentration was to 90%; and, where concentrated to less than 75%, yields were even lower (71.6 vs. 82 or 83 of Examples 1 and 2).

Examples 3 to 6 and Comparatives E and F show the effect of fatty acid to salt of N-methyl taurine ratio. These are set forth below:

2. Effect of Fatty Acid to Salt of N-Methyl Taurine Ratio on Conversion:

| Example # | C12 fatty acid/ taurine ratio | ZnO use % | Taurine salt pre-concentration at 150 C. | Rx temperature (C.) | Rx time (Hr) | % conversion C12 taurate |
|---|---|---|---|---|---|---|
| Comparative E | 1.5 to 1 | 1 | Yes, to 90% | 197 | 1 | 65 |
| Example 3 | 2 to 1 | 1 | Yes, to 90% | 197 | 1 | 83 |
| Example 4 | 3 to 1 | 1 | Yes, to 90% | 197 | 1 | 95 |
| Comparative F | 1.5 to 1 | 0.5 | No, 61% | 195 | 3 | 62.1 |
| Example 5 | 2 to 1 | 0.5 | No, 61% | 195 | 3 | 81.0 |
| Example 6 | 3 to 1 | 0.5 | No, 61% | 195 | 3 | 86.5 |

In Comparative E, neither the ratio of fatty acid to taurine was greater than 1.5 to 1, nor was the reaction time greater than or equal to 2 hours. Yields well below 80 resulted. Comparative F (no pre-concentration) has a ratio of fatty acid to taurine of less than 2 to 1 and attains a low yield of less than 62.1%.

Example 7 and Comparatives G and H show effect of catalyst level. These are set forth below.

3. Effect of Catalyst (e.g., ZnO, Hypophosphorous Acid) Level on Conversion:

| Example # | C12 fatty acid/ taurine ratio | Catalyst use % | Taurine salt pre-concentration at 150 C. | Rx temperature (C.) | Rx time (Hr) | % conversion C12 taurate |
|---|---|---|---|---|---|---|
| Comparative G | 2 to 1 | 0.3 ZnO | No, 61% | 195 | 3 | 72.2 |
| Example 7 | 2 to 1 | 0.5 ZnO | No, 61% | 195 | 3 | 81.0 |
| Example 8 | 2 to 1 | 0.5 $H_3PO_2$ | No, 61% | 195 | 3 | 80.5 |
| Example 9 | 2 to 1 | 0.5 $H_3PO_2$ | No, 61% | 195 | 4 | 89.9 |
| Example 10 | 2 to 1 | 0.5 $H_3PO_4$ | No, 61% | 195 | 4 | 83.4 |
| Comparative H | 2 to 1 | 1 ZnO | No, 61% | 195 | 3 | 68.5 |

These examples related to the aspect of the invention relating to non-concentration.

The examples show sensitivity of reaction to catalyst amount. The catalysts must fall in a range of 0.4 to 0.7 to provide high yield above 80% by wt.; only at a level of 0.5 was yield of 80% or greater obtained.

Examples 11 and 12 and Comparatives I, J and K show the effect of temperature, preferably with regard to browning. These examples are set forth below:

4. Effect of Temperature on Conversion:

| Example # | C12 fatty acid/ taurine ratio | ZnO use % | Taurine salt pre-concentration | Rx temperature (C.) | Rx time (hr.) | % conversion C12 taurate | Product browning |
|---|---|---|---|---|---|---|---|
| Comparative I | 2 to 1 | 1 | Yes, to 90% | 235 | 1 | 60 | Yes, browning |
| Example 11 | 2 to 1 | 1 | Yes, to 90% | 197 | 1 | 83 | No |
| Comparative J | 1.5 to 1 | 1 | Yes, to 90% | 240 | 1 | 52 | Yes, browning |
| Comparative K | 1.5 to 1 | 1 | Yes, to 90% | 225 | 1 | 70 | Yes, browning |
| Example 12 | 3 to 1 | 1 | Yes, to 90% | 195 | 1 | 90 | No |

For best examples of the invention, temperature must be below 200° C., preferably 190 to 199, to ensure undesirable browning is avoided.

The invention claimed is:

1. A process for making alkyl taurate amides which comprises the steps of (1) reacting $C_8$ to $C_{20}$ fatty acid with alkali metal salt of N-methyl taurine, (2) heating the $C_8$ to $C_{20}$ fatty acid with alkali metal salt of N-methyl taurine mixture to a reaction temperature of less than 200° C., (3) adding a catalyst; and (4) stirring the reaction mixture at the temperature of less than 200° C. for two hours or greater, thereby forming the alkyl taurate amides, wherein
    a) the molar ratio of total fatty acid to alkali metal salt, both total fatty acid and salt measured as anhydrous basis, is greater or equal to 2:1; and
    b) the catalyst is used in an amount ranging from 0.4 to 0.7% by wt. based on the total reaction mixture on an anhydrous basis, wherein the catalyst is selected from the group consisting of inorganic zinc compounds; magnesium oxide; phosphoric acid; and mixtures thereof.

2. A process according to claim 1, wherein 50 to 100% of the $C_8$ to $C_{20}$ fatty acid is $C_{12}$.

3. A process according to claim 2, wherein the fatty acid reacted is $C_{10}$ to $C_{14}$ fatty acid.

4. A process according to claim 1, wherein fatty acid is saturated, straight chain fatty acid.

5. A process according to claim 1, wherein the starting the salt taurine salt is not pre-concentrated, by which is meant that salt is not heated to remove water such that the reactant is 75% or more salt.

6. A process according to claim 1, wherein the salt is an aqueous salt solution.

7. A process for making alkyl taurate amide which comprises the steps of (1) pre-concentrating sodium salt of N-methyl taurine salt to at least 75% of taurine salt in water before reacting with fatty acid by heating the sodium salt of N-methyl taurine salt to a temperature of about 150° C. to remove water (2) reacting $C_8$ to $C_{20}$ fatty acid with said sodium salt of N-methyl taurine; (3) heating the $C_8$ to $C_{20}$ fatty acid with alkali metal salt mixture to a reaction temperature of less than 200° C., and (4) adding a catalyst; and (5) stirring the reaction mixture at the temperature of less than 200° C. for less than two hours, thereby forming the alkyl taurate amides, wherein
    a) the molar ratio of fatty acid to salt of N-methyl taurine is greater than 1.5:1;
    b) the catalyst level is 0.1 to 1.5 by wt. based on the total reaction mixture on an anhydrous basis, wherein the catalyst is selected from the group consisting of inorganic zinc compounds; magnesium oxide; phosphoric acid; and mixtures thereof.

8. A process according to claim 7, wherein 50 to 100% of the $C_8$ to $C_{20}$ fatty acid is $C_{12}$.

9. A process according to claim 8, wherein the fatty acid is $C_{10}$ to $C_{14}$ fatty acid.

10. The process according to claim 1, wherein the alkali metal salt is sodium salt of N-methyl taurine.

11. The process according to claim 1, wherein the molar ratio of total fatty acid to alkali metal salt is 2:1 to 5:1.

12. The process according to claim 1, wherein the reaction time temperature is 190 to 199° C.

13. The process according to claim 1, wherein the time of reaction is 2 to 4 hours.

14. The process according to claim 7, wherein the catalyst level is 0. 5 to 1.5% by wt.

15. The process according to claim 14, wherein the catalyst level is 0.8 to 1.2% by wt.

16. The process according to claim 7, wherein the temperature of reaction is 190 to 199° C.

* * * * *